United States Patent [19]

Kirchmayr et al.

[11] 4,279,721
[45] Jul. 21, 1981

[54] MERCAPTOPHENYL KETONES AS INITIATORS FOR THE PHOTOPOLYMERIZATION OF ETHYLENICALLY UNSATURATED COMPOUNDS

[75] Inventors: Rudolf Kirchmayr, Aesch; Louis Felder, Basel, both of Switzerland

[73] Assignee: Ciba-Geigy Corporation, Ardsley, N.Y.

[21] Appl. No.: 39,464

[22] Filed: May 16, 1979

[30] Foreign Application Priority Data

May 23, 1978 [CH] Switzerland ............... 5596/78

[51] Int. Cl.$^3$ ................................. C08F 2/46
[52] U.S. Cl. ................. 204/159.24; 526/208; 526/222; 430/286
[58] Field of Search .............. 204/159.24; 96/115 P

[56] References Cited

U.S. PATENT DOCUMENTS

| | | | |
|---|---|---|---|
| 3,386,904 | 6/1968 | Petropoulos | 204/159.24 |
| 3,720,635 | 3/1973 | Metzner et al. | 204/159.24 |
| 3,759,807 | 9/1973 | Osborn et al. | 204/159.23 |
| 3,903,322 | 9/1975 | Ravve et al. | 204/159.24 |
| 4,054,682 | 10/1977 | Kuesters et al. | 204/159.24 |
| 4,054,684 | 10/1977 | Ceintrey et al. | 427/54 |

Primary Examiner—Harold D. Anderson
Attorney, Agent, or Firm—Luther A. R. Hall

[57] ABSTRACT

Mixtures of (A) a mercaptophenyl ketone of the formula I

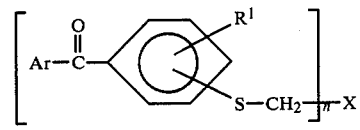

in which n is 1 or 2, Ar is an unsubstituted or substituted aryl radical or a hetero-aromatic radical, $R^1$ is hydrogen, alkyl or, if n is 1, also —$SCH_2X$ and X, if n is 1, is one of the groups —$CH(R^2)$—OH, —$CH(R^2)$—O—CO—$R^5$, —$CH_2SH$ or —$(CH_2)_{1-3}$—$NR^3R^4$, in which $R^2$ is hydrogen, methyl, phenyl or one of the groups —$CH_2OH$, —$CH_2$—$NR^3R^4$ or —$CH_2$—$OR^6$, $R^3$ and $R^4$ independently of one another are hydrogen, alkyl or hydroxyalkyl, or $R^3$ and $R^4$ together are 1,4-butylene, 1,5-pentylene or 3-oxa-1,5-pentylene, and $R^5$ and $R^6$ are monovalent hydrocarbon radicals, and X, if n is 2, is alkylene, vinylene, phenylene or one of the divalent groups —$CH_2S$—$SCH_2$—, —$CH(R^2)$—O—CO—O—$CH(R^2)$—, —$CH(R^2)$—O—CO—$R^7$—CO—$OCH(R^2)$—, —CO—O—$R^8$—O—CO—, —$CH_2COO$—$R^8$—$OOCCH_2$— or —$CH(OH)$—$CH_2$—O—$R^8$—O—$CH_2$—$CH(OH)$—, in which $R^7$ is a divalent hydrocarbon radical or —NH—$R^9$—NH—and $R^8$ and $R^9$ are divalent hydrocarbon radicals, and (B) an organic amine are effective initiators for the photopolymerization of ethylenically unsaturated compounds or for the photochemical crosslinking of polyolefins.

5 Claims, No Drawings

MERCAPTOPHENYL KETONES AS INITIATORS FOR THE PHOTOPOLYMERIZATION OF ETHYLENICALLY UNSATURATED COMPOUNDS

The invention relates to novel initiator mixtures consisting of a mercaptophenyl ketone and an organic amine, for the photopolymerisation of ethylenically unsaturated compounds or for the photochemical cross-linking of polyolefins.

It is known that the photopolymerisation of ethylenically unsaturated compounds can be initiated by aromatic ketones of the benzophenone, anthraquinone, xanthone or thioxanthone type. It is also known from U.S. Pat. No. 3,759,807 that the initiator action of such aromatic ketones can be accelerated by the addition of organic amines. Since these amines on their own usually possess no initiator action, they act, in combination with aromatic ketones, as activators or accelerators. This is of great importance industrially, since the rate of production of photochemically cured coatings or printing pastes is dependent, in particular, on the rate of polymerisation of the unsaturated compounds. Mixtures of aromatic ketones, which contain thioether groups, and organic amines are described as photoinitiators in German Offenlegungsschrift No. 2,602,419. These mixtures have certain advantages over the known mixtures; thus, for example, compared with mixtures of chlorothioxanthone and organic amines they are distinguished by a lesser tendency to yellowing. The thioether-ketones of the said patent specification have the general formula

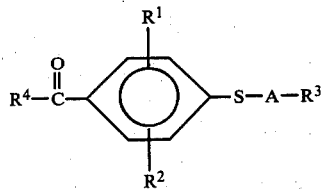

in which $R^4$ is an aromatic or heterocyclic radical, $R^1$ and $R^2$ are hydrogen or monovalent substituents, A can be an alkylene radical and $R^3$ can be hydrogen, aryl, benzoyl, halogen, alkyl, alkoxy, alkylthio, alkoxyalkyl, alkaryl, aralkyl, $NO_2$, CN, COOH or COO-alkyl.

Novel mixtures of aromatic thioether-ketones and organic amines have now been found which, compared with the known mixtures, are distinguished by certain advantages. These advantages can lie in the higher rate of polymerisation, in the lesser tendency to yellowing in the case of white-pigmented coatings, in the better solubility in the substrate or in the increased storage stability.

The invention therefore relates to the use of mixtures of (A) a mercaptophenyl ketone of the formula I

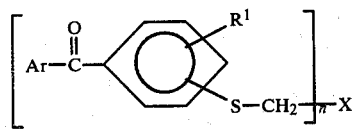

in which n is 1 or 2, Ar is a $C_6$–$C_{10}$ aryl radical, which can be unsubstituted or substituted by one or more of the groups $C_1$–$C_4$ alkyl, phenyl, $C_1$–$C_4$ alkoxy, phenoxy, $C_5$–$C_6$ cycloalkoxy, halogen, —COOH, —COO—($C_1$–$C_4$ alkyl) or benzoyl or, if n is 1, also by —$SCH_2X$, or is a 5-membered or 6-membered hetero-aromatic radical, $R^1$ is hydrogen, $C_1$–$C_4$ alkyl or, if n is 1, also —$SCH_2X$ and X, if n is 1, is one of the groups —CH($R^2$)—OH, —CH($R^2$)—O—CO—$R^5$, —$CH_2SH$ or —$(CH_2)_{1-3}$—$NR^3R^4$, in which $R^2$ is hydrogen, methyl, phenyl or one of the groups —$CH_2OH$, —$CH_2$—$NR^3R^4$ or —$CH_2$—$OR^6$, $R^3$ and $R^4$ independently of one another are hydrogen, $C_1$–$C_8$ alkyl or $C_2$–$C_4$ hydroxyalkyl, or $R^3$ and $R^4$ together are 1,4-butylene, 1,5-pentylene or 3-oxa-1,5-pentylene, $R^5$ is $C_1$–$C_{12}$ alkyl, $C_2$–$C_5$ alkenyl, phenyl, $C_1$–$C_{12}$ alkoxy, phenoxy, —NH—($C_1$–$C_{12}$ alkyl), —NH-phenyl or —NH-cyclohexyl and $R^6$ is $C_4$–$C_{12}$ alkyl or $C_6$–$C_{10}$ aryl, and if n is 2 is a direct bond, $C_1$–$C_6$ alkylene, vinylene, phenylene or one of the divalent groups —$CH_2S$—$SCH_2$—, —CH($R^2$)—O—CO—O—CH($R^2$)—, —CH($R^2$)—O—CO—$R^7$—CO—OCH($R^2$)—, —CO—O—$R^8$—O—CO—, —$CH_2COO$—$R^8$—$OOCCH_2$— or —CH(OH)—$CH_2$—O—$R^8$—O—$CH_2$—CH(OH)—, in which $R^2$ is as defined above, $R^7$ is $C_2$–$C_{10}$ alkylene, vinylene, phenylene or a radical —NH—$R^9$—NH—, $R^8$ is $C_2$–$C_8$ alkylene, phenylene or -phenylene—$C(CH_3)_2$-phenylene and $R^9$ is $C_4$–$C_{10}$ alkylene, $C_6$–$C_{12}$ arylene, tolylene or -phenylene—$CH_2$-phenylene, and (B) an organic amine as initiators for the photopolymerisation of ethylenically unsaturated compounds or for the photochemical crosslinking of polyolefins.

In the indicated formula I, Ar can be a phenyl or naphthyl radical, which can be substituted by substituents such as methyl, ethyl, isopropyl, sec.-butyl, phenyl, methoxy, ethoxy, isopropoxy, phenoxy, cyclopentoxy, cyclohexoxy, F, Cl, Br, —COOH, —$COOCH_3$, —$COOC_2H_5$ or benzyl. If n is 1, Ar can also be an aryl radical substituted by the radical —$SCH_2X$, as a result of which I is a bismercaptoaryl ketone. Ar can also be a hetero-aromatic radical, for example a monovalent pyrrole, thiophen, pyridine or furan radical.

$R^1$ can be H or lower alkyl or, if n is 1, also —$SCH_2X$. In the latter case, two identical thioether groups are present on the phenyl radical.

The position of $R^1$ and —$SCH_2X$ on the phenyl ring is arbitrary and depends on the method of synthesis chosen. Preferably, —$SCH_2X$ is in the 4-position relative to the carbonyl group. The radical —$CH_2X$ located on the sulfur atom is an aliphatic radical which is substituted by at least one hydroxyl, ether, carbamate, ester, thiol or amino group. Examples of amino substituents $R^3$ and $R^4$ are methyl, ethyl, propyl, butyl, hexyl, octyl, 2-ethylhexyl, 2-hydroxyethyl or 2-hydroxypropyl. Examples of the ether radical $R^6$ are butyl, hexyl, octyl, dodecyl, phenyl or naphthyl.

If n is 2, X can be a divalent alkylene radical, for example 1,2-ethylene, 1,3-propylene, 1,4-butylene, 1,6-hexylene or 2-methyl-1,3-propylene. Alkylene $R^7$ can be one of the radicals just mentioned and can also be, for example, octylene, 2,2-diethyl-1,3-propylene or 1,10-decylene. $R^8$ and $R^9$ can likewise be alkylene radicals within the limits of the defined number of carbon atoms. Arylene $R^9$ can be, for example, o-phenylene, p-phenylene or 1,4-naphthylene.

The organic amines used can be aliphatic, aromatic, araliphatic, cycloaliphatic or heterocyclic amines. They can be primary, secondary or tertiary amines; tertiary amines are preferred. Examples are butylamine, dibutylamine, tributylamine, cyclohexylamine, benzyldimethylamine, di-cyclohexylamine, triethanolamine, N-methyldiethanolamine, phenyl-diethanolamine, piperidine, piperazine, morpholine, pyridine, quinoline, ethyl p-dimethylaminobenzoate, butyl p-dimethylaminobenzoate, Michler's ketone (4,4'-bis-dimethylaminobenzophenone) or 4,4'-bis-diethylamino-benzophenone.

Preferred mixtures are those of (A) a mercaptophenyl ketone of the formula I in which n is 1, Ar is phenyl, 2-furyl, 2-thienyl, 2-pyridyl or phenyl which is substituted by $C_1$–$C_4$ alkyl, $C_1$–$C_4$ alkoxy, —$SCH_2X$, —COO—($C_1$–$C_4$ alkyl) or benzoyl, $R^1$ is hydrogen and X is one of the groups —$CH_2OH$, —$CH(CH_3)$—OH, —$CH(OH)_3$—$CH_2OH$, —$CH_2$—$NR^3R^4$ or —$CH_2O$—CO—$R^5$ in which $R^3$ and $R^4$ are $C_1$–$C_4$ alkyl or hydroxyethyl and $R^5$ is $C_1$–$C_4$ alkyl, vinyl or propenyl, and (B) an aliphatic tertiary amine, a alkyl p-dimethylaminobenzoate or Michler's ketone.

Examples of aliphatic tertiary amines are trimethylamine, triethylamine, tri-isopropylamine, tributylamine, dodecyl-dimethylamine, octyl-dimethylamine, triethanolamine, tris-(hydroxypropyl)-amine, N-methyldiethanolamine or N-butyl-diethanolamine.

Particularly preferred mixtures are those of (A) a mercaptophenyl ketone of the formula I in which n is 1, Ar is phenyl, tolyl or xylyl, $R^1$ is hydrogen and X is —$CH_2OH$, —$CH_2NR^3R^4$ or —$CH_2O$—CO—$R^5$, in which $R^3$ and $R^4$ are $C_1$–$C_4$ alkyl, or $R^3$ and $R^4$ together are 1,5-pentylene, and $R^5$ is $C_1$–$C_4$ alkyl or phenyl, and (B) triethanolamine or a $C_1$–$C_4$ alkyl-diethanolamine.

Examples of compounds of the formula I are: 4-(2-hydroxyethyl-mercapto)-benzophenone, 4-(2-acetoxyethyl-mercapto)-benzophenone, 4-(2-benzoyloxyethyl-mercapto)-benzophenone, 4-(2-acryloyloxyethyl-mercapto)-benzophenone, 4-(2-methoxyethyl-mercapto)-benzophenone, 4-(2-aminoethyl-mercapto)-benzophenone, 4-(2-dimethylaminoethyl-mercapto)-benzophenone, 4-(2-diethylaminoethyl-mercapto)-benzophenone, 4-(2-cyclohexylaminoethyl-mercapto)-benzophenone, 4-(3-aminopropyl-mercapto)-benzophenone, 4-(2-morpholinoethyl-mercapto)-benzophenone, 4-(2-hydroxyethyl-mercapto)-4'-methyl-benzophenone, 4-(2-hydroxyethyl-mercapto)-4'-methoxy-benzophenone, 4-(2-hydroxyethyl-mercapto)-4'-phenoxy-benzophenone, 4-(2-hydroxyethyl-mercapto)-2'-carbomethoxy-benzophenone, 4-(2-hydroxyethyl-mercapto)-2'-carbethoxy-benzophenone, 4-(2,3-dihydroxypropyl-mercapto)-benzophenone, 4-[4-(2-hydroxyethyl-mercapto)-benzoyl]-biphenyl, 1-[4-(2-hydroxyethyl-mercapto)-benzoyl]-naphthalene, 2-[4-(2-hydroxyethyl-mercapto)-benzoyl]-napthalene, 1,2-di-[(4-benzoylphenyl)-mercapto]-ethane, 1,2-di-[(4-benzoylphenyl)-mercapto]-xylylene and di-[2-(4-benzoylphenyl-mercapto)-ethyl] carbonate.

The compounds of the formula I are novel compounds. They can be prepared in various ways. For example, mercaptophenyl ketones of the formula II

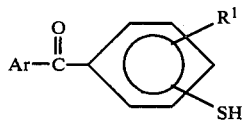

or their alkali metal salts can be reacted with halogenoalkyl compounds of the formula Hal—$CH_2$—X or Hal—$CH_2$—X—$CH_2$—Hal, in which formulae Hal is chlorine, bromine or iodine and Ar, $R^1$ and X are as defined for formula I.

However, the compounds of the formula II can also be reacted with epoxides or glycidyl ethers, in which case compounds of the formula I are formed in which X is —$CH(R^2)OH$. By reacting these compounds with conventional acylating agents, for example with carboxylic acid chlorides or carboxylic acid anhydrides, compounds of the formula I are obtained in which X is —$CH_2(R^2)$—O—CO—$R^5$ or —$CH(R^2)$—OOC—$R^7$—COO—$CH(R^2)$—.

Furthermore, the compounds of the formula I can be reacted with epichlorohydrin and the resulting chlorohydrin converted, using primary or secondary amines, alkali metal alcoholates or aqueous alkali, to the compounds of the formula I in which $R^2$ is —$CH_2OH$, —$CH_2NR^3R^4$ or —$CH_2OR^6$.

The reaction of compounds of the formula I with difunctional compounds, for example with diglycidyl ethers, to give compounds of the formula I in which n is 2 proceeds analogously.

In a second important method of preparation, aromatic halogenoketones of the formula III

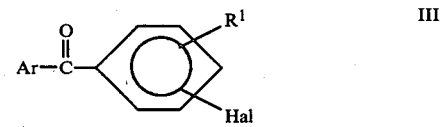

are used as the starting materials and these are reacted with a mercaptan of the formula HS—$CH_2X$ or HS—$CH_2$—X—$CH_2$—SH, or with the alkali metal compounds thereof. The hydroxyalkylmercaptans HS—$CH_2CH(R^2)$—OH are particularly suitable for this purpose. The hydroxy compounds of the formula I, X=—$CH_2(R^2)OH$, which thus form can, in a subsequent reaction, be reacted in a conventional manner with mono- or di-functional acylating agents or isocyanates.

A further method of preparation is a Friedel-Crafts reaction with components which already contain the group —S—$CH_2X$, i.e., for example, the reaction of an acid chloride Ar—COCl with a compound of the formula IV

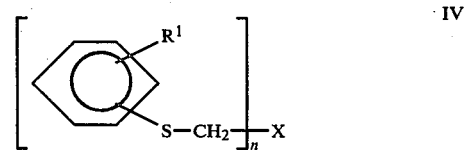

in the presence of aluminium chloride.

The mixtures according to the invention contain the compounds of the formula I and the organic amines in a weight ratio of 4:1 to 1:4.

According to the invention, the mixtures are used as initiators for the photopolymerisation of ethylenically unsaturated compounds or of systems which contain such compounds.

Photopolymerisable compounds of this type are, for example, unsaturated monomers, such as esters of acrylic or methacrylic acid, for example methyl acrylate, ethyl acrylate, n- or tert.-butyl acrylate, isooctyl acrylate or hydroxyethyl acrylate, methyl methacrylate or ethyl methacrylate, ethylene diacrylate, butanediol diacrylate, hexanediol diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide and N-substituted (meth)-acrylamides; vinyl esters, for example vinyl acetate, vinyl propionate, vinyl acrylate or vinyl succinate; other vinyl compounds, such as vinyl ethers, vinyl ketones, vinylsulfones, styrene, alkylstyrenes, halogenostyrenes, divinylbenzene, N,N'-divinylurea, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether, and the mixtures of such unsaturated monomers.

Further photopolymerisable compounds are unsaturated oligomers or polymers and their mixtures with unsaturated monomers. These include, for example, unsaturated polyesters, prepared from phthalic acid and maleic acid or fumaric acid with diols, such as ethylene glycol, propylene glycol, butanediol or neopentyl glycol, and their mixtures with styrene.

Further examples are unsaturated acrylic resins. These include, for example, reaction products of polyepoxides (epoxy resins) with acrylic acid or methacrylic acid or reaction products of polyisocyanates with hydroxyalkyl acrylates and also the reaction products of hydroxyl group-containing polyesters or polyethers with acrylic acid or methacrylic acid. These unsaturated acrylic resins are in most cases used as a mixture with one or more acrylates of a mono-, di- or poly-alcohol, for example ethyl acrylate, butyl acrylate, benzyl acrylate, 2-ethylhexyl acrylate or 2-hydroxypropyl acrylate, ethylene glycol diacrylate, propylene glycol diacrylate, butanediol diacrylate, hexamethylene diacrylate, trimethylolpropane trisacrylate or pentaerythritol tetraacrylate.

Photopolymerisable systems such as are used for the various purposes usually contain a number of other additives in addition to the photopolymerisable compounds and the photoinitiator. Thus, it is frequently customary to add thermal inhibitors, which are intended, in particular, to guard against premature polymerisation during the preparation of the systems by mixing the components. Substances used for this purpose are, for example, hydroquinone, hydroquinone derivatives, p-methoxyphenol or β-naphthols. Furthermore, small amounts of UV absorbers can be added, for example those of the benzotriazole or benzophenone type.

Photopolymerisable systems also contain—depending on the intended use—fillers, such as silica, talc or gypsum, pigments, dyes, agents which impart thixotropic properties or flow control agents, such as silicone oil. Photopolymerisable systems can also contain small amounts of solvents.

Furthermore, combinations with known photoinitiators which form free radicals by photofragmentation, for example benzoin ethers, dialkoxyacetophenones or benzil ketals, can also be used.

The initiator mixtures according to the invention are of great importance for the photo-curing of printing pastes, since the drying time of the binder is a decisive factor for the rate of production of graphical products and should be of the order of magnitude of fractions of a second. The initiators according to the invention are also very suitable for photo-curable systems for the preparation of printing plates.

A further field of application is the UV-curing of metal coatings, for example in the lacquer coating of sheet metal for tubes, cans or bottle closures, and also the UV-curing of plastic coatings, for example of floor or wall coverings based on PVC.

Examples of the UV-curing of paper coatings are the colourless lacquer coating of labels, gramophone record sleeves or book jackets.

The mixtures according to the invention can also be used as initiators for the photochemical crosslinking of polyolefins. Such polyolefins are, for example, polypropylene, polybutene, polyisobutylene and also copolymers, for example ethylene/propylene copolymers, but preferably polyethylene of low, medium or high density.

For the fields of application mentioned, the initiator mixtures according to the invention are suitably used in amounts of 0.5 to 20% by weight and preferably of about 1 to 5% by weight, based on the photopolymerisable or crosslinkable system. In this context, system is to be understood as meaning the mixture of the photopolymerisable or crosslinkable compound, the photoinitiator and the other fillers and additives which is used for the particular application.

The addition of the photoinitiators to the photopolymerisable systems is generally effected by simple stirring in, since most of these systems are liquid or readily soluble. Usually the initiators according to the invention dissolve and this ensures uniform distribution and transparency of the polymers.

The polymerisation is effected by the known methods of photopolymerisation, by irradiation with light, which is rich in short-wave radiation. Suitable light sources are, for example, medium-pressure, high-pressure and low-pressure mercury lamps and also superactinic fluorescent tubes, the emission maxima of which are in the range between 250 and 400μ.

For photochemical crosslinking of polyolefins, the photoinitiator is added to the polyolefin before or during the shaping processing, for example by mixing in powder form or by mixing with the plasticised polyolefin.

Crosslinking is effected by irradiating the shaped article in the solid form, for example in the form of films or fibres.

The examples which follow describe the preparation of compounds of the formula I and the use of their mixtures with organic amines as photoinitiators. Parts and percentages are by weight. Temperatures are given in °C.

EXAMPLE 1

4-(2-Hydroxyethyl-mercapto)-benzophenone (a) 17.2 g (0.225 mol) of 2-mercaptoethanol and 15 g (0.225 mol) of KOH (85% pure) in 200 ml of toluene are refluxed for 1½ hours under nitrogen under a water separator. The water separated off is discarded. The toluene is distilled off. 48.8 g (0.225 mol) of 4-chlorobenzophenone and 150 ml of dimethylacetamide are added to the solidified potassium salt. The mixture is stirred at 100° C. for 5 hours. The reaction mixture is poured onto water and neutralised with acetic acid. The product is taken up in ether. The ether layer is washed with water, dried over $Na_2SO_4$ and concentrated. The resulting product is boiled up with hexane and the crystals are collected. Yield: 44 g (76%). Melting point 49°–52°.

$C_{15}H_{14}O_2S$ Calculated: C 69.74; H 5.46; S 12.41%; (258.34) Found: C 69.9; H 5.8; S 12.7%.

(b) 11.2 g (0.05 mol) of 4-chlorobenzophenone, 4.3 g (0.055 mol) of 2-mercaptoethanol, 13.8 g (0.1 mol) of calcined $K_2CO_3$ and 15 ml of ethyl methyl ketone are warmed (under reflux) for 16 hours under nitrogen. 50 ml of water are poured over the cooled reaction mixture and the resulting mixture is acidified with HCl. The product is taken up in ether. The ether layer is washed with water, dried over $Na_2SO_4$ and concentrated. The product, which in this case also is obtained in the form of an oil, crystallises on standing. It is boiled up in hexane as described under (a). Yield: 10.1 g (77%). Melting point 49°-51°.

EXAMPLES 2-4

Esters of 4-(2-hydroxyethyl-mercapto)-benzophenone

General method:

Esterification is in each case carried out with the corresponding acid chloride in tetrahydrofuran, with the addition of 1 equivalent of diisopropylethylamine. After the reaction has ended, the tetrahydrofuran is removed. Water is poured over the residue and the mixture is extracted with ether. The ether layer is washed with water, dried over $Na_2SO_4$ and concentrated. The resulting crude products are in each case purified through a silica gel dry column (solvent system: ethyl acetate/hexane, 1:4, or $CH_2Cl_2$). Yield: 71-74% in each case.

(2) 4-(2-Acetoxyethyl-mercapto)-benzophenone: melting point 36°-39°.

$C_{17}H_{16}O_3S$ Calculated: C 67.98; H 5.37; S 10.68%; (300.37) Found: C 67.9; H 5.5; S 10.6%.

(3) 4-(2-Benzoyloxyethyl-mercapto)-benzophenone: oil.

$C_{22}H_{18}O_2S$ Calculated: C 72.91; H 5.01; S 8.85%. (362.44) Found: C 73.0; H 5.1; S 8.5%.

(4) 4-(2-Acryloxyethyl-mercapto)-benzophenone: oil.

$C_{18}H_{16}O_3S$ Calculated: C 69.21; H 5.16; S 10.27%; (312.38) Found: C 68.9; H 5.4; S 10.4%.

EXAMPLE 5

A blue printing paste is prepared in accordance with the following recipe: 55.0 parts by weight of Setalin AP 560 (acrylic resin from Synthese, Holland), 20.0 parts by weight of Irgalith GLSM (blue pigment from Ciba-Geigy), 4.0 parts by weight of photoinitiator of the formula I, 4.0 parts by weight of N-methyldiethanolamine and 17.0 parts by weight of Ebecryl 150 (acrylic resin from UCB Belgium).

A blue colour paste is prepared from the Setalin AP 560 and the Irgalith GLSM in a ball mill.

The photo-curing agent is pre-dissolved with the amine in Ebecryl 150 and incorporated in the blue colour paste by dispersing on a muller. The printing paste is then applied in an amount of 2 g/m² to special paper with the aid of a Prüfbau proof apparatus.

Printing conditions: Contact pressure: 25 Kp/cm²; Printing speed: 2 m/seconds.

Immediately after printing, the samples are cured in one pass by irradiating in a UV apparatus (manufacturer: Radiation Polymer Company USA) at variable transport speed.

Apparatus conditons: power of the lamp; 80 W/cm (standard mercury vapour lamp); distance from the lamp; 11 cm.

The set-off test is used to assess the curing. With this test the speed is determined at which no further transfer of the printing paste to neutral paper can be detected under a constant pressure of 25 Kp/cm². The abrasion test with a Rel-Scratch-Hardness-Recorder according to Defense Specification DES No. 1053 method No. 8 is also carried out. The table given below lists the measured values found with the benzophenone derivatives according to the invention. The figures in the second column indicate the printing speed in m/seconds which is possible if no transfer of the printing paste is to be obtained in the set-off test. The higher this speed, the more rapid is the curing of the printing paste. The figures in the third column indicate the speed at which the abrasion test is passed.

Printing or curing speed in m/seconds.

| Initiator used | Set-off test | REL test |
|---|---|---|
| Compound No. 1 | 2.00 | 1.25 |
| Compound No. 2 | 1.5 | 1.25 |
| Compound No. 3 | 1.5 | 1.0 |
| Compound No. 4 | 1.75 | 1.0 |

EXAMPLES 6-13

4'-(2-Hydroxyethyl-mercapto)-3,4-dimethyl-benzophenone 12.2 g (0.05 mol) of 4'-chloro-3,4-dimethylbenzophenone and 4.3 g (0.055 mol) of 2-mercaptoethanol in 50 ml of dimethylacetamide are heated to 95° under nitrogen. 13.8 g (0.1 mol) of calcined $K_2CO_3$ are then added. The suspension is kept at 90°-100° C. for 6 hours. 100 ml of water are poured over the resulting reaction mixture and the mixture is extracted with ether. The ether layer is washed with water, dried over $Na_2SO_4$ and concentrated. The crystals obtained are recrystallised from methanol and dried in vacuo at 60° C. Yield: 10.1 g (71%). Melting point 92°-93° C.

$C_{17}H_{18}O_2S$ Calculated: C 71.30; H 6.34; S 11.19%; (286.39) Found: C 71.4; H 6.3; S 11.1%.

Further benzophenone derivatives are prepared in the same way. The resulting crude products are recrystallised from a suitable solvent and in some cases also purified through a silica gel dry column (solvent system: chloroform/ethanol, 95:5).

TABLE 1

Compounds of the formula Ar—CO—⟨C₆H₄⟩—S—CH₂CH₂OH

| Example No. | Ar | Melting point | Analysis (calculated/found) C | H | S |
|---|---|---|---|---|---|
| 6 | 3,4-dimethylphenyl (CH₃, CH₃-) | 92–93° | 71.3/71.4 | 6.34/6.3 | 11.10/11.1 |
| 7 | 2,4-dimethylphenyl (CH₃, CH₃-) | 64–66° (ligroin) | 73.1/71.4 | 6.34/6.2 | 11.19/11.1 |
| 8 | 2,5-dimethylphenyl (CH₃, CH₃-) | oil | 71.3/71.1 | 6.34/6.4 | 11.19/10.5 |
| 9 | 4-methylphenyl (CH₃-⟨⟩-) | 99° (acetonitrile) | 70.56/70.7 | 5.92/6.0 | 11.77/11.6 |
| 10 | 4-methoxyphenyl (CH₃O-⟨⟩-) | 102° (ethanol) | 66.65/66.2 | 5.59/5.6 | 11.12/11.0 |
| 11 | 4-isopropylphenyl (CH₃)₂CH-⟨⟩- | 56° | 71.97/71.7 | 6.71/6.7 | 10.47/10.5 |
| 12 | 2-thienyl | 65° | 59.06/58.6 | 4.58/4.5 | 24.26/24.3 |
| 13 | 4-phenoxyphenyl (⟨⟩-O-⟨⟩-) | 122–124° | 71.98/71.6 | 5.18/5.1 | 9.15/9.1 |

EXAMPLES 14–17

4-(2-N,N-Dimethylaminoethyl-mercapto)-benzophenone 12.85 g (0.064 mol) of 4-chlorobenzophenone, 13.6 g (0.13 mol) of 2-N,N-dimethylaminoethanethiol and 27.6 g (0.2 mol) of potassium carbonate in 100 ml of N,N-dimethylacetamide are kept at 100° C. for 12 hours under N₂ gas and with stirring. After cooling, the reaction mixture is poured into 200 ml of water. The oil which separates out is taken up in ether. The crude product is purified by means of an extraction with hydrochloric acid and distillation in a ball tube (bath 200°–220° C./0.01 mm Hg). The yield is 10.2 g (59%) of product, which is obtained in the form of an oil.

The following compounds were obtained analogously:

(15) 2-(2-Hydroxyethyl-mercapto)-4'-methyl-benzophenone. Viscous oil. Analysis (calculated/found): C 70.56/69.5%, H 5.92/6.2%, O 11.75/11.7%, S 11.77/12.5%.

(16) 2-(2-Hydroxyethyl-mercapto)-benzophenone. Oil. Analysis (calculated/found): C 69.74/68.9%, H 5.46/5.5%, S 12.41/13.5%.

(17) 4-(2,3-Dihydroxypropyl-mercapto)-benzophenone. Melting point 86°–88°.

EXAMPLE 18

A blue printing paste is prepared in accordance with the following recipe: 165 parts of Setalin AP 560 (acrylic resin from Synthese, Holland), 45 parts of Farbenruss 2/0 (gas black from Degussa, Frankfurt/Main), 15 parts of Vossenblau 360 (blue pigment from Degussa, Frankfurt/Main) and 27 parts of Ebecryl 150 (acrylic resin from UCB Belgium).

These components are mixed to a paste and mixed three times on a three-roll mill.

4.6 parts of the blue printing paste according to the above recipe, 0.2 part of photoinitiator and 0.2 part of triethanolamine are added together and the mixture is homogenised on a muller. The printing paste is then applied in an amount of 1.5 g/m² to special paper with the aid of a Prüfbau proof apparatus.

Printing conditions: Contact pressure; 100 Kp/cm²; Application speed; 1 m/second.

Immediately after printing, the samples are cured in one pass by irradiation in a UV apparatus (manufacturer: Radiation Polymer Company USA) at variable transport speed.

Apparatus conditions: Power of the lamp; 80 W/cm (standard mercury vapour lamp); Distance from the lamp; 11 cm.

The set-off test is used to assess the curing. In this test the speed is determined at which, under a contact pressure of 100 Kp/cm², no further transfer of the printing paste to neutral paper can be detected. The abrasion test with a Rel-Scratch-Hardness-Recorder according to Defense Specification No. DES-1053 Method No. 8 is also carried out. The table which follows lists the measured values found for the benzophenone derivatives according to the invention. The figures in the second column indicate the maximum printing speed in m/minute which is possible if no transfer of the printing paste is to take place in the set-off test. The higher this speed, the more rapid is the curing of the printing paste. The figures in the third column indicate the speed at which the abrasion test is passed.

TABLE 2

| Initiator used | Set-off test | REL test |
| --- | --- | --- |
| | Printing or curing speed in m/minute | |
| Benzophenone | 15 | 5 |
| Compound No. 1 | 45 | 15 |
| Compound No. 6 | 45 | 15 |
| Compound No. 7 | 45 | 15 |
| Compound No. 9 | 45 | 15 |
| Compound No. 10 | 45 | 30 |
| Compound No. 11 | 30 | 30 |
| Compound No. 13 | 30 | 15 |

What is claimed is:

1. A photopolymerizable composition comprising (a) at least one ethylenically unsaturated compound; and (b) a mixture in a 4:1 to 1:4 ratio by weight of a compound of formula I

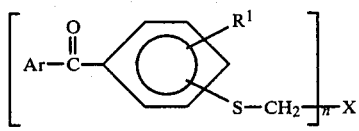

in which n is 1, Ar is phenyl, 2-furyl, 2-thienyl, 2-pyridyl or phenyl which is substituted by $C_1$-$C_4$ alkyl, $C_1$-$C_4$ alkoxy, —COO— ($C_1$-$C_4$ alkyl), —SCH$_2$X or benzoyl, $R^1$ is hydrogen and X is one of the groups —CH$_2$OH, —CH(CH$_3$)—OH, —CH(OH)—CH$_2$OH, —CH$_2$—NR$^3$R$^4$ or —CH$_2$—O—CO—R$^5$, in which $R^3$ and $R^4$ are $C_1$-$C_4$ alkyl or hydroxyethyl, or together are 1,5-pentylene, and $R^5$ is $C_1$-$C_4$ alkyl, phenyl, vinyl or propenyl, with an organic amine; and wherein the amount of component (b) is from 0.5 to 20% by weight of total composition.

2. A composition according to claim 1 where in the compound of formula I n is 1, Ar is phenyl, tolyl or xylyl, $R^1$ is hydrogen and X is —CH$_2$OH, —CH$_2$NR$^3$R$^4$ or —CH$_2$O—CO—R$^5$, in which $R^3$ and $R^4$ are methyl or ethyl or together are 1,5-pentylene and $R^5$ is $C_1$-$C_4$ alkyl or phenyl.

3. A composition according to claim 1 where the compound of compound I is 4-(2-hydroxyethylmercapto)benzophenone or a carboxylic acid ester thereof.

4. A composition according to claim 1 in which component (a) is an acrylic acid ester or a mixture of several acrylic acid esters.

5. A composition according to claim 1 which is a printing paste.

* * * * *